Figure 1:
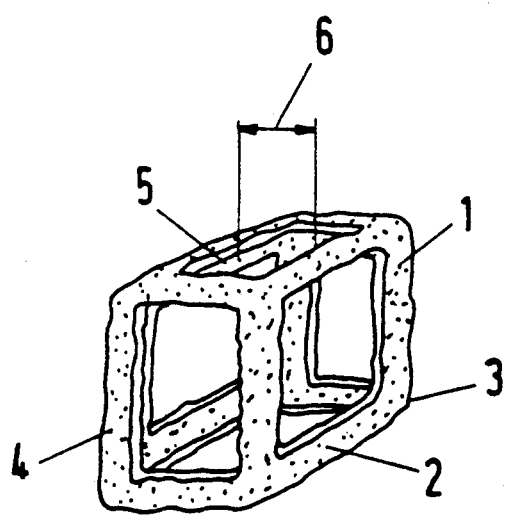

United States Patent

Bohler et al.

[11] Patent Number: 5,147,402
[45] Date of Patent: Sep. 15, 1992

[54] IMPLANT FOR INGROWTH OF OSSEOUS TISSUE

[75] Inventors: Nikolaus Bohler, Linz, Austria; Rudolf Koch, Berlingen, Switzerland

[73] Assignee: Sulzer Brothers Limited, Winterthur, Switzerland

[21] Appl. No.: 784,896

[22] Filed: Oct. 30, 1991

[30] Foreign Application Priority Data

Dec. 5, 1990 [CH] Switzerland ............... 3845/90

[51] Int. Cl.⁵ .................. A61F 2/28; A61B 17/56; A61B 17/58
[52] U.S. Cl. ........................ 623/16; 623/17; 606/60; 606/61
[58] Field of Search ................... 623/16-18; 606/60, 61, 62, 64

[56] References Cited

U.S. PATENT DOCUMENTS

| | | |
|---|---|---|
| 4,743,256 | 5/1988 | Brantigan ............. 623/16 X |
| 4,820,305 | 4/1989 | Harms et al. ........ 623/17 X |
| 4,878,915 | 11/1989 | Brantigan .............. 623/17 |

FOREIGN PATENT DOCUMENTS

| | | |
|---|---|---|
| 0307241 | 3/1989 | European Pat. Off. . |
| 0328847 | 8/1989 | European Pat. Off. . |
| 2910627 | 9/1980 | Fed. Rep. of Germany ........ 623/16 |

Primary Examiner—Ronald Frinks
Attorney, Agent, or Firm—Kenyon & Kenyon

[57] ABSTRACT

An implant for ingrowth of osseous tissue is constructed of a hollow skeletal three-dimensional support member having a plurality of openings for the ingrowth of osseous tissue into an interior cavity. The surfaces of the beams defining the openings may also be roughened to promote the fusion of tissue.

1 Claim, 1 Drawing Sheet

IMPLANT FOR INGROWTH OF OSSEOUS TISSUE

This invention relates to an implant and particularly to an implant for ingrowth of osseous tissue.

Heretofore, as described in European Patent Application 0328847, implants have been known for use in supplementing a pelvic bone which can be implanted together with an artificial acetabulum. As described, the implant is preformed for the insertion site or is deformable during an operation and is filled with bone splinters and placed on the pelvic bone so as to guarantee the fusion of bone splinters. However, such an implant is usually specifically constructed for a specific use.

It is an object of the invention to improve the process of spongiosa grafting with an implant which is universally applicable.

It is another object of the invention to provide an implant of relatively simple construction which can be implanted in a bone to promote the ingrowth of osseous tissue.

Briefly, the invention provides an implant for ingrowth of osseous tissue which is comprised of a hollow skeletal three-dimensional support member, for example, made of titanium, and which has a plurality of interconnected beams defining at least one opening in each wall of the support member for an ingrowth of osseous tissue into an interior cavity. In addition, each beam has a roughened surface while the openings or windows defined by the beams are of more than three millimeters in diameter so as to permit the interior cavity of the support member to become filled with homologous or autologous osseous tissue parts.

One of the advantages of the implant is that a plurality of such implants can be created which can adhere to the healthy bone in a variable arrangement and which become interconnected before being filled with splinters of bone and becoming wedged. Another advantage is that the inserted implant can transmit pressure loads from the very outset without the support member deviating from the intended shape.

These and other objects and advantages of the invention will become more apparent from the following detailed description taken in conjunction with the accompanying drawing wherein:

FIG. 1 illustrates a perspective view of an implant constructed in accordance with the invention.

Referring to FIG. 1, the implant for promoting the ingrowth of osseous tissue is comprised of a hollow skeletal three-dimensional support member 1, for example, being formed from a hollow block of titanium. In addition, the support member has a plurality of interconnected beams 2 which are connected at points of intersection 3 and which define a plurality of openings or windows 5 into the interior cavity of the support member 1. In this respect, there is an opening 5 in each wall of the support member 1 and each opening 5 has an aperture 6 which is of a minimum diameter of three millimeters so that the interior of the support member 1 can be filled with osseous tissue.

As illustrated, the support member is of cubic shape and the outside surfaces of the beams 2 have a roughened surface 4 to promote the fusion of the osseous tissue.

The support member 1 can be attached to osseous tissue in the region of implant by means of suitable attachment means, such as U-shaped nails and staples or may be secured in place with wire. In addition, the space in and around a plurality of implanted support members 1 may be wedged with splinters of bone (not shown).

The construction of the support members is such as to protect the osseous tissue growing on the original bone from inadmissable loads by its dimensional stability.

In one embodiment, a plurality of support members 1 can be placed within a suitable implant site in a bone with splinters of bone being wedged around the support members. Initially, ingrowing osseous tissue will fuse to the roughened surfaces 4 of the support members 1 and, thereafter, homologous or autologous parts of osseous tissue will pass into the interior cavities of the elements via the openings 5.

The invention thus provides an implant which can be universally applied for the grafting of spongiosa on bones.

Further, the invention provides an implant which is able to transmit pressure loads from very outset of implantation without deviation from an intended shape.

Preferred embodiments of the invention have the outside dimensions of a cube with an edge length of 12 to 30 mm, which has been shortened in one main axis by 30 to 60 percent, whereas the thickness of the beams 2 varies between 2 and 3 mm. Access has to be from all sides for the stuffing with bone chips and for the growing connection between bone and bone chips. Anyone of the 6 limiting planes of the support member 1 can be the mating surface to the bone (not shown).

What is claimed is:

1. An implant for ingrowth of osseous tissue comprising a hollow skeletal three-dimensional cubic shaped support member having a plurality of interconnected beams defining at least one opening in each wall of said member for an ingrowth of osseous tissue into an interior cavity, each said beam having a roughened surface and each said opening having a diameter greater than 3 millimeters, and wherein said support member is made of titanium.

* * * * *